(12) United States Patent
Sliwinski et al.

(10) Patent No.: US 9,345,256 B2
(45) Date of Patent: *May 24, 2016

(54) HIGH ENERGY LIQUID ENTERAL NUTRITIONAL COMPOSITION

(71) Applicant: N.V. Nutricia, Zoetermeer (NL)

(72) Inventors: Edward Lucian Sliwinski, Oss (NL); Wynette Hermina Agnes Kiers, Heteren (NL); Natalie Elizabeth Hotrum, Bennekom (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/632,918

(22) Filed: Feb. 26, 2015

(65) Prior Publication Data

US 2015/0164122 A1    Jun. 18, 2015

Related U.S. Application Data

(63) Continuation of application No. 13/843,330, filed on Mar. 15, 2013, now Pat. No. 8,999,423, which is a continuation of application No. 12/746,490, filed as application No. PCT/NL2008/050777 on Dec. 5, 2008, now Pat. No. 8,409,651.

(60) Provisional application No. 61/059,865, filed on Jun. 9, 2008.

(30) Foreign Application Priority Data

| Dec. 5, 2007 | (WO) | PCT/NL2007/050626 |
| Jun. 9, 2008 | (EP) | 08157877 |
| Nov. 14, 2008 | (EP) | 08169152 |

(51) Int. Cl.
   A23L 1/29      (2006.01)
   A23L 1/305    (2006.01)
   A23L 1/308    (2006.01)

(52) U.S. Cl.
   CPC ............ *A23L 1/296* (2013.01); *A23L 1/308* (2013.01); *A23L 1/3056* (2013.01); *A23V 2002/00* (2013.01)

(58) Field of Classification Search
   CPC .................................. A23L 1/29; A23L 1/308
   USPC ................. 426/573, 580, 583, 601, 656, 658
   See application file for complete search history.

(56) References Cited

U.S. PATENT DOCUMENTS

| 3,764,711 A | 10/1973 | Melnychyn et al. |
| 3,843,828 A | 10/1974 | Arndt |
| 4,112,123 A | 9/1978 | Roberts |
| 4,497,836 A | 2/1985 | Marquardt et al. |
| 5,256,437 A | 10/1993 | Degen et al. |
| 5,514,655 A | 5/1996 | DeWille et al. |
| 5,641,531 A | 6/1997 | Liebrecht et al. |
| 5,683,984 A | 11/1997 | Jost |
| 5,780,039 A | 7/1998 | Greenberg et al. |
| 5,948,452 A | 9/1999 | Monte |
| 6,383,551 B1 | 5/2002 | Foegeding et al. |
| 6,774,111 B1 | 8/2004 | Wolf et al. |
| 7,247,320 B2 | 7/2007 | Jost |
| 7,858,028 B2 | 12/2010 | Pijls |
| 7,868,042 B2 | 1/2011 | Romanczyk et al. |
| 8,409,651 B2 | 4/2013 | Sliwinski et al. |
| 2003/0022863 A1 | 1/2003 | Stahl et al. |
| 2003/0077357 A1 | 4/2003 | Rizvi et al. |
| 2003/0099761 A1 | 5/2003 | Jost |
| 2004/0057867 A1 | 3/2004 | Pijls |
| 2004/0258823 A1 | 12/2004 | Dufresne et al. |
| 2006/0051296 A1 | 3/2006 | Holahan |
| 2007/0104760 A1 | 5/2007 | Yokawa et al. |
| 2007/0128341 A1 | 6/2007 | Bakkene et al. |
| 2007/0154614 A1 | 7/2007 | Sherwood et al. |
| 2007/0202153 A1 | 8/2007 | Molenaar |
| 2009/0162494 A1 | 6/2009 | Lai |
| 2010/0216740 A1 | 8/2010 | Stahl et al. |
| 2010/0286020 A1 | 11/2010 | Calame et al. |
| 2014/0011742 A1 | 1/2014 | Sedman et al. |

FOREIGN PATENT DOCUMENTS

| AU | 2172288 B | 3/1989 |
| EP | 0 322 96 | 7/1981 |
| EP | 0 833 27 | 7/1983 |
| EP | 0 323 529 A1 | 7/1989 |
| EP | 0 438 783 A2 | 7/1991 |
| EP | 0 486 425 A2 | 5/1992 |
| EP | 0 686 396 B1 | 1/1995 |
| EP | 0 747 395 A1 | 12/1996 |
| EP | 1 151 754 B1 | 11/2001 |
| EP | 1 314 361 A1 | 5/2003 |

(Continued)

OTHER PUBLICATIONS

"Enhanced weight gain system, advanced recovery formula drink mix" Elite Image Nutrition, [Online] 2002, XP002515496—Retrieved from the Internet: http://www.beverlyintl.com/weight-gainer-massmaker.html> [retrieved on Feb. 17, 2009], 4 pages.
"Evaluation and Definition of Potentially Hazardous Foods—Chapter 3. Factors that influence Microbial Growth", Safe Practices for Food Processes (Auszug Internet FDA), 2014.
"Milk Protein Concentrate Ingredients," [Online] 2003, Retrieved from the Internet: http://www.innovatewithdiary.com/NR/rdonlyres/37F8B376-A74F-4DE6-BC8F-3B238A823A95/0/G5IngredientSpecMPC.pdf> retrieved on Feb. 20, 2009, pp. 1-2, XP002516236.
"Muscle Milk, Nature's Ultimate Growth Formula" IFAST400 Monster Maker, [Online] Jul. 23, 2003, Retrieved from the Internet: http://www.1fast400.com/p433_Mass_Maker_Beverly_International.html>, retrieved on Feb. 20, 2009, pp. 1-3, XP002516238.
Aerosol—Wikipedia—http://en.wikipedia.org/wiki/Aerosol, dated Jan. 6, 2014.

(Continued)

Primary Examiner — Helen F Heggestad
(74) Attorney, Agent, or Firm — Foley & Lardner LLP; Sunit Talapatra

(57) ABSTRACT

High energy and high protein liquid nutrition enteral compositions are provided that contain micellar casein and caseinate, an optionally a small amount of whey.

32 Claims, No Drawings

(56) References Cited

FOREIGN PATENT DOCUMENTS

| | | |
|---|---|---|
| EP | 1 351 587 A1 | 10/2003 |
| EP | 1 563 741 A1 | 8/2005 |
| EP | 1 654 934 A1 | 5/2006 |
| EP | 1 351 587 B1 | 9/2006 |
| EP | 1 787 528 A1 | 5/2007 |
| EP | 1 839 492 B1 | 10/2007 |
| EP | 2 230 941 A1 | 9/2010 |
| EP | 2 612 561 A1 | 7/2013 |
| GB | 1 277 772 | 6/1972 |
| JP | 11-018723 | 1/1999 |
| WO | WO-93/03754 | 3/1993 |
| WO | WO-93/08697 | 5/1993 |
| WO | WO-95/17830 | 7/1995 |
| WO | WO-97/11614 | 4/1997 |
| WO | WO-98/07328 | 2/1998 |
| WO | WO-99/56563 | 11/1999 |
| WO | WO-01/60378 A2 | 8/2001 |
| WO | WO-02/15720 A2 | 2/2002 |
| WO | WO-02/052166 | 7/2002 |
| WO | WO-02/098242 A1 | 12/2002 |
| WO | WO-03/043446 | 5/2003 |
| WO | WO-03/055334 A1 | 7/2003 |
| WO | WO-03/084340 A1 | 10/2003 |
| WO | WO-2004/054371 A2 | 7/2004 |
| WO | WO-2004/060342 | 7/2004 |
| WO | WO-2005/039597 A2 | 5/2005 |
| WO | WO-2005/082170 A1 | 9/2005 |
| WO | WO-2006/034857 | 4/2006 |
| WO | WO-2006/042222 | 4/2006 |
| WO | WO-2006/058083 A2 | 6/2006 |
| WO | WO-2006/058538 A1 | 6/2006 |
| WO | WO-2006/120155 A1 | 11/2006 |
| WO | WO-2007/027213 A1 | 3/2007 |
| WO | WO-2007/047592 | 4/2007 |
| WO | WO-2007/082267 | 7/2007 |
| WO | WO-2007/108827 A1 | 9/2007 |
| WO | WO-2007/110411 A2 | 10/2007 |
| WO | WO-2007/110421 A2 | 10/2007 |
| WO | WO-2007/136263 | 11/2007 |
| WO | WO-2008/041219 A1 | 4/2008 |
| WO | WO-2008/136420 A1 | 11/2008 |
| WO | WO-2009/011573 A1 | 1/2009 |
| WO | WO-2009/072869 A1 | 6/2009 |
| WO | WO-2009/072884 A1 | 6/2009 |
| WO | WO-2009/072886 A1 | 6/2009 |
| WO | WO-2009/113845 A1 | 9/2009 |
| WO | WO-2009/113858 A1 | 9/2009 |
| WO | WO-2009/150183 | 12/2009 |

OTHER PUBLICATIONS

Affirmation of Alistair James Carr, dated Dec. 24, 2013, 10 pgs.
Affirmation of Stephen Murray Taylor, dated Dec. 24, 2013, 10 pgs.
Alizadehfard, M. et al. "Viscosity of Whey Protein Solutions", Iranian J Polymer Science and Technology, 1995, vol. 4, No. 2, pp. 126-133.
Anonymous, "Nepro Specialized Complete Balanced Nutrition," date unknown, found at http://rpdcon40.ross.com/mn/ . . . /C668F1C5D1267DF105256CDE0048A266?OpenDocumen, 8 pages.
Anonymous, "Nestle VHC (Very High Calorie) 2.25 Carnation Instant Breakfast, Lactose Free," date unknown, retrived from internet, www.vitalitymedical.com/nestle-vhc-very-high-calorie-2-25-carnation-instant-breakfast-lactose-free, 5 pages.
Anonymous, "Pro-Cal Shot," date unknown, retrieved from internet, www.vitafloweb.com, 2 pages.
Arla Foods—Wikipedia—http://en.wikipedia.org/wiki/Arla_Foods, dated Dec. 17, 2013.
BiPRO—"Whey Protein Isolate"—Davisco Foods International, Inc., date unknown.
Bipro—"whey protein isolate"—Jan. 6, 2014, (https://www.google.de/search?q=Bipro %22whey protein isolate%22 filetype%3A).
Burrington, "High-Powered Protein Drinks," Food Product Design [Online], Oct. 1, 2001: http://www.foodproductdesign.com/articles/2001/10/high-powered------protein-drinks.aspx.
Chantrapornchai, et al. "Influence of a NaCl on optical properties, large-strain rheology and water holding capacity of heat-induced whey protein isolate gels", Food Hydrocolloids, 2002, vol. 16, pp. 467-476.
Chen, J. et al. "Viscoelastic Properties of Heat-Set Whey Protein Emulsion Gels", Journal of Texture Studies, 1998, vol. 29, pp. 285-304.
Demetriades, K. et al. "Influence of pH and Heating on Physicochemical properties of Whey Protein-Stabilized Emulsions Containing a Nonionic Surfactant", J. Agric. Food Chem., 1998, vol. 46, pp. 3936-3942.
Demetriades, K. et al. "Physical Properties of Whey Protein Stabilized Emulsions as Related to pH and NaCl", Journal of Food Science, 1997, vol. 62, No. 2, pp. 342-347.
Dewan et al., "Viscosity and Voluminosity of Bovine Milk Casein Micelles", Department of Biochemistry,Department of Food Science and Industries, University of Minnesota, Jun. 30, 1972, pp. 699-705, 7 pages.
Dunford, "Sports Nutrition: A Practice Manual for Professionals," 4th Ed., 2006, pp. 130-131 (best available copy—view at http://www.google.com/search?tbm=bks&hl=en&q=marie+dunford+increasing+casein+protein+and+health+benefits&btnG=).
Eilers, "Die Viskosität von Emulsionen hochviskoser Stoffe als Funktion der Konzentration," Kolloid Z, 1941, 97(3)313-321.
Euston, S. et al. "Aggregation kinetics of heated whey protein-stabilized emulsions", Food Hydrocolloids, 2000, vol. 14, pp. 155-161.
Ferreira et al., "Instrumental Method for Characterizing Protein Foams," J Food Sci, 1995, 60(1):90-93.
Foegeding, E. et al. "Factors that determine the fracture properties and microstructure of globular protein gels", Food Hydrocolloids, 1995, vol. 9, No. 4, pp. 237-249.
Hunt, J. et al. "Heat Stability of Oil-in-Water Emulsions Containing Milk Proteins: Effect of Ionic Strength and pH", Journal of Food Science, 1995, vol. 60, No. 5, pp. 1120-1131.
International Preliminary Report on Patentability for PCT/NL2008/050776, dated Mar. 18, 2010.
International Search Report for PCT/NL2008/050141, mailed Nov. 14, 2008.
International Search Report for PCT/NL2008/050776, mailed Mar. 17, 2009.
International Search Report for PCT/NL2009/050120, mailed Jul. 9, 2009.
International Search Report in PCT/NL2007/050626, dated Oct. 29, 2008.
International Search Report in PCT/NL2008/050777, mailed Mar. 23, 2009.
International Search Report in PCT/NL2011/050390 dated Mar. 8, 2011.
Karlsson et al., "Relataionship Between Physical Properties of Casein Micelles and Rheology of Skim Milk Concentrate," J. Dairy Sci., vol. 88, Nov. 1, 2005, pp. 3784-3797, 14 pages.
Marshall, K. "Therapeutic Applications of Whey Protein", Alternative Medicine Review, 2004, vol. 9, No. 2, pp. 136-156.
McDougall et al., "The Whey Proteins of the Milk of Red Deer (Cervus elaphus L.), A Homologue of Bovine β-Lactoglobulin," Biochem. J., vol. 153, Mar. 1, 1976, pp. 647-655.
Melo et al., Effect of Ultra-High-Temperature Steam Injection on Model Systems of α-Lactalbumin and β-Lactoglobulin, J Dairy Sci, 1978, 61(6):710-713.
Milch—Wikipedia—http://de.wikipedia.org/wiki/Milch, dated Jan. 6, 2014.
Milk protein concentrate—Wikipedia—http://en.wikipedia.org/wiki/Milk_protein_concentrate, dated Jan. 6, 2014.
Monkos, "Determination of Some Hydrodynamic Parameters of Ovine Serum Albumin Solutions Using Viscometric Measurements," J Biol Phys, 2005, 31(2):219-232.
Monkos, "On the Hydrodynamics of Dimeric Bovine Beta-Lactoglobulin Solutions from Viscometry Approach," Polish J. of Environ. Stud., vol. 15, No. 4A, Sep. 20, 2006, pp. 88-90.

(56) References Cited

OTHER PUBLICATIONS

Notice of Opposition (Arta Foods Amba) in EP Appln No. 09718670.4 dated Jan. 10, 2014.
Notice of Opposition (Fonterra Co-Operative Group Limited) in EP Appln No. 09718670.4 dated Jan. 9, 2014.
Notice of Opposition (Friesland Brands B.V.) in EP Appln No. 09718670.4 dated Jan. 10, 2014.
Notice of Opposition (Nestec SA) in EP Appln No. 09718670.4 dated Jan. 10, 2014.
Pap, et al. "Waste minimization and utilization in the food industry: Processing of arctic berries, and extraction of valuable compounds from juice-processing by-products", Jun. 10, 2004, University of Oulu, Finland, Oulu University Press: Oulu pp. 159-168.
Parker et al., "Effects of Added Sodium Caseinate on the Formation of Particles in Heated Milk," J Agric Food Chem, 2005, 53(21):8265-8272.
Pasteurisierung—Wikipedia—http://de.wikipedia.org/wiki/Pasteurisierung, dated Dec. 11, 2013.
Sodinin et al., "Milk and milk-based dairy ingredients," Manufacturing Yogurt and Fermented Milks 2006, pp. 167-178, Blackwell Publishing [XP002497557] [on line url:http://books.google.nl/books?id=lroZmON2tHsC&pg=PA167&lpg=PA167&dq=sodini,milk-based dairy ingredients&source=web&ots=SpCQK9-5Zy&sig=ydp-1P7trkP40Eosf7Sbt6LzDPQ&h1=en&sa=X&oi=book_result&resnum=1&ct=result>.
Souci, et al.—"Food composition and Nutrition Tables", MedPharm Scientific Publishers, 2008, 171-174.
Spagnuolo PA et al., Kappa-carrageenan interactions in systems containing casein micelles and polysaccharide stabilizers. Food Hydrocolloids, Elsevier, vol. 19, No. 3, May 1, 2005.
Transmittal and International Preliminary Report on Patentability for PCT/NL2009/050120, dated May 11, 2010.
Velez-Ruiz et al, "Rheological Properties of Concentrated Milk as a Function of Concentration, Temperature and Storage Time," J Food Eng, 1998, 35:177-190.
Walstra et al."Dairy Science and Technology," 2nd Ed,The Free Library. Retrieved Jan. 21, 2011 from http://www.thefreelibrary.com/Dairy+science+and+technology,+2d+ed.-a0139423256.
Whey protein—Wikipedia, Oct. 16, 2013, 3 pgs.
Wijesinha-Bettoni, R. et al. "Heat Treatment of Bovine alpha-Lactalbumin Results in Partially Folded, Disulfide Bond Shuffled States with Enhanced Surface Activity", Biochemistry, 2007, vol. 46, pp. 9774-9784.
Written Opinion and Search Report mailed Apr. 8, 2009 in International Application No. PCT/NL2008/050778.
Ye, A. et al. "Characterization of cold-set gels produced from heated emulsions stabilized by whey protein", International Dairy Journal, 2009, vol. 19, pp. 721-727.
Zayas, "Functionality of Proteins in Food", Springer-Verlag Berlin Heidelberg GmbH, 1997, Chapter 1.

HIGH ENERGY LIQUID ENTERAL NUTRITIONAL COMPOSITION

CROSS-REFERENCE TO RELATED APPLICATIONS

This is a continuation of U.S. application Ser. No. 13/843,330, filed Mar. 15, 2013, now U.S. Pat. No. 8,999,423, which is a continuation of U.S. application Ser. No. 12/746,490, now U.S. Pat. No. 8,409,651, filed as a National Stage application of PCT/NL2008/050777, filed Dec. 5, 2008, which claims the benefit and priority of International Application No. PCT/NL2007/050626, filed Dec. 5, 2007; European Patent Application No. 08157877.5, filed Jun. 9, 2008; U.S. Provisional Application No. 61/059,865, filed Jun. 9, 2008; and European Patent Application No. 08169152.9, filed Nov. 14, 2008. The foregoing applications are incorporated by reference herein in their entirety.

FIELD OF THE INVENTION

The present invention is in the field of liquid enteral nutritional compositions.

BACKGROUND OF THE INVENTION

The present invention relates in general to a liquid enteral composition for providing nutrition, either as a supplement, or as a complete nutrition, with a high energy content.

The human body requires energy to perform its vital functions, such as blood circulation, immune processes, respiration processes, etc. Energy can be supplied in the form of calories. Calories are typically supplied by the consumption of food. Calorie sources can be classified into three categories: proteins, fats, and carbohydrates. Proteins can provide the body with support for muscular activity, fats can provide the body with stored energy, and carbohydrates can supply the body with immediate energy. Essential vitamins and minerals are necessary to help regulate the processes of the human body.

A person should receive a proper balance of nutrients to sustain health, otherwise, malnutrition can result in a variety of physical complications. Moreover, it is imperative that the support provided be adapted to the needs of a person. For example, patients who are ill, require increased and specialized nutritional support. An increase in specific nutrients can help the body recover from a particular stress placed upon it, such as sport, emotional and labour stress, illness, medical surgery, malnutrition, etc.

Nutritional needs can also change with a person's age. For example, elderly persons show a decrease in the amount of energy their body requires from fat sources.

In this respect, it is submitted that in the context of this application, an elderly person is a person of the age of 50 or more, in particular of the age of 55 or more, more in particular of the age of 60 or more, more in particular of the age of 65 or more. This rather broad definition takes into account the fact that the average age varies between different populations, on different continents, etc. Most developed world countries have accepted the chronological age of 65 years as a definition of 'elderly' or older person (associated with the age at which one may begin to receive pension benefits), but like many westernized concepts, this does not adapt well to e.g. the situation in Africa. At the moment, there is no United Nations (UN) standard numerical criterion, but the UN agreed cut-off is 60+ years to refer to the older population in Western world. The more traditional African definitions of an elder or 'elderly' person correlate with the chronological ages of 50 to 65 years, depending on the setting, the region and the country.

Because at least certain persons may not receive their required nutritional support from a normal diet, or may not be able to eat normal food, nutritional compositions, such as nutritional supplements and complete nutrition have been designed to provide nutritional support to persons in need thereof. This nutrition can be directed towards a particular type of nutritional support. For example, a supplement may provide a person with additional calories for increased energy. Although these supplements provide a certain amount of nutritional support, it is in the best interests to provide a nutritional composition having increased nutritional value for a specific nutritional requirement. In the above examples of elderly persons and ill patients, it is desired to provide nutritional liquid compositions having increased energy as well as increased protein per unit dosage.

In this regard, although an elderly person's energy needs may be reduced, their ability to consume products may also be diminished. For example, they may have difficulty consuming a product due to, e.g., swallowing difficulties, or due the too large amount of product they need to consume to meet the daily intake of nutrients. Hence, compliance is not optimal, and often, the intake is suboptimal, leading to suboptimal nourishment.

Further, certain disease states or conditions may require restrictions on the diet a patient consumes. For example, renal patients may have fluid restrictive diets.

Also, a number of patients need nutrition in the smallest volume of liquid. These patients may be cachectic patients or persons suffering from end-stage AIDS, cancer or cancer treatment, severe pulmonary diseases like COPD (Chronic Obstructive Pulmonary Disease), tuberculosis and other infection diseases or persons that experience severe surgery or trauma like burns. Furthermore, persons suffering from disorders in the throat or mouth such as oesophageal cancer or stomatitis and persons having problems with swallowing like dysphagic persons, require special liquid, low-volume nutrition. Also, persons suffering from reduced appetite and/or loss of taste will benefit from a low-volume liquid nutritional composition.

Therefore, a need exists for improved enteral compositions, with an increased amount of protein and calories per unit volume for an elderly person or ill patient.

However, increasing calories and/or proteins in a nutritional liquid composition may increase the overall viscosity of the composition. This can make the liquid nutritional composition difficult to consume or administer, and can also diminish the taste of the nutritional composition. Furthermore, technical difficulties exist in producing a stable, in particular a shelf-stable nutritional liquid composition having a high content of proteins.

The problem of the present invention is therefore to provide a stable, attractive, liquid enteral composition for providing nutrition, either as a supplement, or as a complete nutrition, with a high energy content, to a person, in particular to an elderly person or an ill patient.

PRIOR ART

WO 02/098242 A1 (Nestlé, 12 Dec. 2002) discloses a calorically dense liquid oral supplement (2.25 kcal/ml) based on a (60:40) soy protein isolate/caseinate mixture with a protein level of 9 g/100 ml (16 En %), 12.25 g/100 ml of fat (49 En %), and 19.7 g/100 ml of digestible carbohydrates (35 En %).

U.S. Pat. No. 5,683,984 (Nestec S.A.) and the corresponding EP patent 0 686 396 B1 teach to replace all of the caseinate in a medium energy nutritional formulation (1 kcal/ml) by native micellar casein to obtain a formulation essentially containing native micellar casein with a low viscosity and a thermal stability to withstand sterilization. It discloses a composition containing a maximum of 7 vol % of native micellar casein. However, the latter document does not teach to replace only part of the caseinate by native micellar casein in a high energy high protein nutritional formulation and the problems that would arise in doing so, nor does it teach the poor shelf and heat stability, nor measures to overcome said problems with the formulations according to our invention.

The commercially available product RESOURCE® 2.0 is a high calorie product from Novartis (2 kcal/ml), based on a mixture of calcium and sodium caseinate as protein source, comprising 9 g/100 ml of proteins (18 En %), 8.7 g/100 ml of fat (39 En %), and 21.4 g/100 ml of digestible carbohydrates (43 En %), and is provided in a 237 ml unit dosage.

The commercially available product VHC® 2.25 is a high calorie product from Nestlé (2.25 kcal/ml), based on a mixture of calcium- and potassium caseinate and isolated soy protein as protein source, comprising 9 g/100 ml of proteins (16 En %), 12 g/100 ml of fat (48 En %) and 19.7 g/100 ml of digestible carbohydrates (35 En %), and is provided in a 250 ml unit dosage.

The commercially available product FRESUBIN® 2.0 is a high calorie product from Fresenius (2 kcal/ml), based on milk proteins as protein source, comprising 10 g/100 ml of proteins (20 En %), 7.8 g/100 ml of fat (35 En %), and 22.5 g/100 ml of digestible carbohydrates (45 En %), and is provided in a 200 ml unit dosage.

The commercially available product PRO-CAL SHOT® is a high calorie product from Vitaflo International Ltd (3.34 kcal/ml), based on skimmed milk powder and sodium caseinate as protein source, comprising 6.7 g/100 ml of proteins (8 En %), 28.2 g/100 ml of fat (76 En %), and 13.4 g/100 ml of digestible carbohydrates (16 En %), and is provided in a 250 ml unit dosage.

The commercially available product TwoCal® HN is a high calorie product from Abbott Laboratories (Ross Nutrition) (2 kcal/ml), based on sodium and calcium caseinate as protein source, comprising 8.4 g/100 ml of proteins (16.7 En %), 8.9 g/100 ml of fat (40.1 En %), and 21.6 g/100 ml of digestible carbohydrates (43.2 En %), and is provided in a 237 ml unit dosage.

SUMMARY OF THE INVENTION

The present invention provides a liquid enteral nutritional composition with a high energy content, designed to meet the nutritional needs of persons in need thereof, in particular elderly and patients with certain disease states. The composition provides an increased amount of energy per unit volume while providing a sufficiently low viscosity to allow the composition to be easily consumed orally or be administered by tube. In addition, the taste of the composition is not diminished.

To this end, in a first aspect of the present invention, a liquid enteral nutritional composition is provided comprising 6 to 14 g of protein per 100 ml of the composition, said protein including micellar casein and caseinate, the composition having an energy density of at least 2.0 kcal/ml.

In a specific embodiment, a liquid enteral nutritional composition is provided comprising 6 to 14 g of protein per 100 ml of the composition, said protein including micellar casein, caseinate and whey, the composition having an energy density of at least 2.0 kcal/ml.

In particular, a liquid enteral nutritional composition is provided comprising protein that provides 10% to 30% of the total energy content of the composition, said protein including micellar casein and caseinate, the composition having an energy density of at least 2.0 kcal/ml.

In a specific embodiment, a liquid enteral nutritional composition is provided comprising protein that provides 10% to 30% of the total energy content of the composition, said protein including micellar casein, caseinate and whey, the composition having an energy density of at least 2.0 kcal/ml.

Micellar casein, also named native micellar casein, is a high quality milk protein and naturally occurring in milk in a concentration of about 2.6 g/100 ml (Dairy Science and Technology, Walstra et al., CRC Press, 2006). It is concentrated by a process that does not, or does not substantially denature the casein proteins and it is marketed as Micellar Casein Isolate (MCI). Fresh skim milk is subjected to a filtration process, in much the same process used to concentrate whey protein, to produce a pure, substantially undenatured milk protein with its native structure. The resulting material contains more than 95 weight % micellar casein, the rest mainly being whey protein and other non-protein nitrogen and other constituents, such as lactose. It has an intrinsic low viscosity and a liquid composition comprising said MCI is therefore easy to drink.

In contrast, casein, as it is used in the context of this invention refers to the curd form of casein, having lost its native micellar structure.

Within the context of this invention, it is understood that micellar casein may also be provided by other milk protein sources, such as, for instance, sources with essentially preserve the natural 80:20 ratio of casein to whey, such as Milk Protein Concentrate (MPC), which is a powder product usually prepared by ultrafiltration with an average protein content of about 80 weight %, Milk Protein Isolate (MPI), a powder product usually prepared by precipitation with an average protein content of more than 85 weight %, and skimmed concentrated milk.

Although the composition of the present embodiment should not contain large amounts of proteins other than micellar casein and caseinate, it was found that the composition of the present invention may comprise up to about 30 weight % of whey protein based on total protein without substantially affecting the viscosity and shelf-stability, even after pasteurisation and/or sterilisation.

A problem associated with the use of micellar casein in the production of liquid enteral nutritional compositions with a high protein content and further containing acids, in particular citric acid, is the formation of calcium-acid complexes, such as calcium citrate. In particular citric acid is added to the composition to adjust the pH and also to adjust Ca-ion activity. A certain Ca-ion activity is beneficial to maintain a desired viscosity of the composition during processing of the composition, e.g. during pasteurisation and/or sterilisation. Calcium, originating from the micellar casein tends to react with acid, in particular the citric acid, thus forming calcium citrate crystals, which precipitate when the acidity of the composition increases over time (pH lowering), giving rise to a poor shelf stability. Already at a pH of 6.9, the formation of Ca-citrate crystals is progressing. On the other hand, a certain Ca-ion activity is beneficial to maintain a desired viscosity of the composition during processing of the composition, e.g. during pasteurisation and/or sterilisation. In particular a certain Ca-ion activity is beneficial to prevent a viscosity increase during heating. Thus, besides shelf stability, it is a problem to arrive at a proper viscosity when using micellar casein. These problems have now surprisingly been solved by the inventors by a mixture of micellar casein and caseinate. Surprisingly, the viscosity of the final composition is not increased as much as could be expected by the substitution of an amount of micellar casein by the same amount of caseinate, such that a composition is obtained after heat-treatment with still a low viscosity, which is still very easy to drink or to administer by tubing, while at the same time no undesired Ca-acid precipitates are observed. By heat-treatment is meant any common treatment known to the skilled person to pasteurise or sterilise the composition of the present invention, in the manufacture of a nutritional composition, such as defined below.

In a second aspect, the present invention concerns a method of providing nutrition to a person in need thereof, comprising the steps of administering to said person the nutritional composition according to the present invention.

In a third aspect, the present invention concerns the use of a mixture of micellar casein and, caseinate, and according to a specific embodiment micellar casein, caseinate and whey in the manufacture of a liquid nutritional composition according to the present invention for providing nutrition to a person.

The invention will now be further elucidated by describing the preferred embodiments of the present invention.

DETAILED DESCRIPTION OF THE INVENTION

Protein

According to one embodiment of the present invention, a liquid enteral nutritional composition is provided comprising 6 to 14 g of protein per 100 ml of the composition, preferably 8 to 14 g/100 ml of the composition, more preferably 8 to 12 g/100 ml of the composition, said protein including micellar casein and caseinate, in particular micellar casein, caseinate and whey, the composition having an energy density of at least 2.0 kcal/ml.

According to another embodiment of the present invention, the protein provides 10% to 30%, preferably 12% to 20%, more preferably 14% to 18%, at least 15% of the total energy content of the composition. The % of total energy is also abbreviated as En %; En % is thus short for energy percentage and represents the relative amount that a constituent contributes to the total caloric value of the composition. In another embodiment of the present invention, the protein provides at least 16% of the total energy content. The high levels of protein are beneficial for patients who may not be physically capable of receiving a large volume, for example, fluid restricted patients. Such patients can be given a reduced level of fluid while still receiving a required amount of nutritional support per day.

In the context of this application, the term "at least" also includes the starting point of the open range. For example, an amount of "at least 95 weight %" means any amount equal to 95 weight % or above.

In the context of this application, enteral means orally or by tube.

In the context of this application, the nutritional composition according to the invention is heat-treated in order to make the composition suitable for commercial use, i.e. the nutritional composition according to the invention is subjected to a heat-treatment such as pasteurisation or sterilisation such that the microbacterial load is reduced.

In one embodiment of the present invention, the composition has an energy density of at least 2.0 kcal/ml, preferably at least 2.2 kcal/ml, more preferably at least 2.3 kcal/ml, even more preferably at least 2.4 kcal/ml. Although the composition has a high energy density, it also has a sufficiently low viscosity to allow it to be consumed by persons that may have difficulty swallowing products or those that are tube fed.

In one embodiment of the present invention, the combined amount of micellar casein and caseinate in the liquid nutritional composition according to the invention is at least 70 weight %, more preferably at least 85 weight %, more preferably at least 90 weight %, more preferably at least 95 weight % of the total protein present in the liquid nutritional composition.

In another embodiment of the present invention, the combined amount of micellar casein, caseinate and whey in the liquid nutritional composition according to the invention is at least 90 weight %, more preferably at least 95 weight % of the total protein present in the liquid nutritional composition.

As aforementioned, the composition of the present invention should not contain large amounts of proteins other than micellar casein and caseinate. However, in a further embodiment of the present invention, the composition may comprise up to about 30 weight % of whey, or less than or equal to 20 weight % of whey, or less than or equal to 15 weight % of whey, or less than or equal to 5 weight % of whey of the total protein present in the liquid nutritional composition.

In one embodiment of the present invention, Na-caseinate, Mg-caseinate, K-caseinate, Ca-caseinate or any mixture thereof or combinations thereof such as Na/K-caseinate and Na/Mg caseinate are used as the source of caseinate. Preferably, Ca-caseinate, or a caseinate comprising Ca is not used, as the micellar casein already contains a sufficient amount of calcium, and the formation of further calcium crystals should be avoided.

In one embodiment of the present invention, the weight ratio of micellar casein to caseinate ranges from 90:10 to 35:65. Preferably, the weight ratio of micellar casein to caseinate ranges from 80:20 to 40:60.

In another embodiment of the present invention when also an amount of whey is present, the weight ratio of micellar casein to whey ranges from 95:5 to 70:30. Preferably, the weight ratio of micellar casein to whey is equal to about 80:20.

The composition according to the invention is designed to either supplement a person's diet or to provide complete nutritional support. Hence, the composition according to the invention may further comprise at least fat and/or carbohydrate and/or a source of vitamins and minerals and/or a source of prebiotics. Preferably, the composition according the invention is a nutritionally complete composition.

Fat

In one embodiment of the present invention, the liquid nutritional composition according to the invention further comprises fat, said fat providing between 20 to 40% of the total energy content of the composition. For a 2.0 kcal/ml composition, this amounts to 40 to 80 kcal per 100 ml.

With regard to the type of fat, a wide choice is possible, as long as the fat is of food quality.

The fat may either be an animal fat or a vegetable fat or both. Although animal fats such as lard or butter have essentially equal caloric and nutritional values and can be used interchangeably, vegetable oils are highly preferred in the practice of the present invention due to their readily availability, ease of formulation, absence of cholesterol and lower concentration of saturated fatty acids. In one embodiment, the present composition comprises rapeseed oil, corn oil and/or sunflower oil.

The fat may include a source of medium chain fatty acids, such as medium chain triglycerides (MCT, mainly 8 to 10 carbon atoms long), a source of long chain fatty acids, such as long chain triglycerides (LCT) and phospholipid-bound fatty acids such as phospholipid-bound EPA or DHA, or any combination of the two types of sources. MCTs are beneficial because they are easily absorbed and metabolized in a metabolically-stressed patient. Moreover, the use of MCTs will reduce the risk of nutrient malabsorption. LCT sources, such as canola oil, rapeseed oil, sunflower oil, soybean oil, olive oil, coconut oil, palm oil, linseed oil, marine oil or corn oil are beneficial because it is known that LCTs may modulate the immune response in the human body.

In one specific embodiment, the fat comprises 30 to 60 weight % of animal, algal or fungal fat, 40 to 70 weight % of vegetable fat and optionally 0 to 20 weight % of MCTs based on total fat of the composition. The animal fat preferably comprises a low amount of milk fat, i.e. lower than 6 weight %, especially lower than 3 weight % based on total fat. In particular, a mixture of corn oil, egg oil, and/or canola oil and specific amounts of marine oil are used. Egg oils, fish oils and algal oils are a preferred source of non-vegetable fats. Especially for compositions that are to be consumed orally, in order to prevent formation of off-flavours and to decrease a fishy after-taste, it is recommended to select ingredients that are relatively low in docosahexanoic acid (DHA), i.e. less than 6 weight %, preferably less than 4 weight % based on total fat. Marine oils containing DHA are preferably present in the composition according to the invention in an amount lower than 25 weight %, preferably lower than 15 weight % based on total fat. On the other hand, inclusion of eicosapentanoic acid (EPA) is highly desirable for obtaining the maximum health effect. Therefore, in another embodiment, the amount of EPA may range between 4 weight % and 15 weight %, more preferably between 8 weight % and 13 weight % based on total fat. The weight ratio EPA:DHA is advantageously at least 6:4, for example between 2:1 and 10:1. In yet another embodiment, the amount of EPA is very low, such as 0.1 to 1 weight %, preferably 0.3 weight % or 0.6 weight %, based on total fat.

Also, the liquid nutritional composition according to the invention may beneficially comprise an emulsifier. Commonly known emulsifiers may be used and generally the emulsifier contributes to the energy content of the fat in said composition.

Digestible Carbohydrate

In one embodiment of the present invention, the liquid nutritional composition according to the invention further comprises digestible carbohydrate, said digestible carbohydrate providing between 30 to 60% of the total energy content of the composition. For a 2.0 kcal/ml composition, this amounts to 80 to 120 kcal per 100 ml. Preferably, the digestible carbohydrate provides at least 40% of the total energy content of the composition according to the invention. The digestible carbohydrate may comprise either simple or complex carbohydrates, or any mixture thereof. Suitable for use in the present invention are glucose, fructose, sucrose, lactose, trehalose, palatinose, corn syrup, malt, maltose, isomaltose, partially hydrolysed corn starch, maltodextrins, glucose oligo- and poly-saccharides.

The composition of the digestible carbohydrate preferably is such that high viscosities, excessive sweetness, excessive browning (Maillard reactions) and excessive osmolarities are avoided. Acceptable viscosities and osmolarities may be achieved by adjusting the average chain length (average degree of polymerisation, DP) of the digestible carbohydrates between 1.5 and 6, preferably between 1.8 and 4. In order to avoid excessive sweetness, the total level of sucrose and fructose is less than 52% and preferably less than 40% of the weight of the carbohydrate, especially of the digestible carbohydrate. Long-chain digestible carbohydrates such as starch, starch fractions and mild starch hydrolysates (DP≥6, DE<20), may also be present, preferably in an amount of less than 25 weight %, especially less than 15 weight % of the digestible carbohydrate, and less than 6 g/100 ml, preferably less than 4 g/100 ml of the total liquid enteral composition according to the invention.

In one embodiment of the present invention, the digestible carbohydrate includes maltodextrose with a high DE (dextrose equivalent). In one embodiment the digestible carbohydrate includes maltodextrose with a DE of >20, preferably >30 or even >40, such as a DE of about 47. Surprisingly, the use of maltodextrose leads to few or no Maillard reaction products upon heating. Without being bound to any explanation, this effect might be attributed to the fact that the compact micellar structure of the micellar casein offers few lysine reaction sites for a Maillard reaction. In one embodiment of the present invention, the digestible carbohydrate includes maltodextrose with a high DE in an amount of at least 35 weight %, preferably at least 50 weight %, preferably at least 65 weight %, preferably at least 90 weight % of the total weight of digestible carbohydrate. In one embodiment of the present invention, the digestible carbohydrate includes maltodextrose with a low DE of 2 to 20. In one embodiment of the present invention, the digestible carbohydrate includes maltodextrose with a low DE of 2 to 10, preferably with a low DE of about 2. In one embodiment of the present invention, the digestible carbohydrate includes maltodextrose with a low DE in an amount of less than 35 weight %, preferably less than 20 weight %, preferably less than 10 weight % of the digestible carbohydrate. Maltodextrose with a low DE may also be referred to as maltodextrine. In another embodiment of the present invention, the digestible carbohydrate includes maltodextrose with a high DE, preferably a DE of >20, preferably >30 or even >40, most preferably a DE of about 47 in combination with maltodextrose with a low DE, preferably a low DE of 2 to 20, more preferably a low DE of 2 to 10, most preferably with a low DE of about 2. As is known, maltodextrose with a low DE, such as of about 2, gives rise to a high viscosity. Maltodextrose with a high DE, such as of about 47 gives rise to a low viscosity, but is very sweet. The combination of both maltodextroses optimizes the balance between sweetness and viscosity. In one embodiment of the present invention, the digestible carbohydrate includes at least 65 weight %, preferably at least 90 weight %, based on total weight of digestible carbohydrate of maltodextrose with a DE>40, preferably with a DE of about 47 and 0 to 10 weight % of maltodextrose with a DE 2 to 10, preferably with a DE of about 2.

In another embodiment of the present invention, the digestible carbohydrate includes trehalose. As was indicated, it is one of the main objects of the invention to provide a nutritional composition with a low viscosity. Sucrose is very well suited for such purpose, but gives rise to very sweet compositions, which are in general disliked by the consumer. Maltodextrose with a low DE, such as of about 2, does not suffer from the latter drawback, but gives rise to a high viscosity. Maltodextrose with a high DE, such as of about 47 gives rise to a low viscosity, but is again very sweet, and gives further rise to the undesired Maillard reactions. Trehalose is a preferred choice of digestible carbohydrate, as it gives rise to a low viscosity, no undesired Maillard reactions and it has a sweetness about half of that of sucrose. In one embodiment of the present invention, the digestible carbohydrate includes trehalose in an amount of 20% to 60% of the weight of the digestible carbohydrate, in an amount of 20% to 45%, more preferably in an amount of 25% to 45% of the weight of the digestible carbohydrate.

Vitamins and Minerals

The composition according to the invention may contain a variety of vitamins and minerals. Overall, the composition according to the invention preferably includes at least 100% of the United States Recommended Daily Allowance (US-RDA) of vitamins and minerals in a one liter portion.

In one embodiment of the present invention, the composition according to the invention provides all necessary vitamins and minerals. For example, the composition according to the invention preferably provides 6 mg of zinc per 100 ml of the composition which is beneficial for tissue repair in a healing patient. Preferably, the composition according to the invention (also) provides 25 mg of vitamin C per 100 ml of the composition to aid patients with more severe healing requirements. Further, preferably, the composition according to the invention (also) provides 2.25 mg iron per 100 ml of the composition. Iron is beneficial in maintaining bodily fluids as well as circulatory system functions in an elderly patient.

In another embodiment of the present invention, the amount of divalent ions ranges between 170 mg/100 ml and 230 mg/100 ml and preferably between 180 mg/100 ml and 220 mg/100 ml. Preferably, the amount of calcium ranges between 155 mg/100 ml and 185 mg/100 ml and preferably between 160 mg/100 ml and 180 mg/100 ml. The phosphorus content can be above 10 mg per g of protein, with a calcium to phosphorus weight ratio between 1.0 and 2.0, preferably between 1.1 and 1.7. Carnitin may advantageously be present in an amount of 8 mg/100 ml to 1000 mg/100 ml, preferably 10 mg/100 ml to 100 mg/100 ml of composition; it may have the form of carnitin, alkyl carnitin, acyl carnation or mixtures thereof. Organic acids are preferably present at a level of between 0.1 g/100 ml to 0.6 g/100 ml, especially 0.25 g/100 ml to 0.5 g/100 ml. These acids include short fatty acids such as acetic acid, hydroxy acids such as lactic acid, gluconic acid, and preferably polyvalent hydroxy acids, such as malic acid and citric acid. In one embodiment of the present invention, the present composition also comprises citric acid.

Non-Digestible Carbohydrates

The liquid enteral nutritional composition according to the invention may optionally be fortified with non-digestible carbohydrates (dietary fibres) such as fructo-oligosaccharides or inulin. In an embodiment of the present invention, the composition according to the invention comprises 0.5 g/100 ml to 6 g/100 ml of non-digestible carbohydrates. The dietary fibres include non-digestible oligosaccharides having a DP of 2 to 20, preferably 2 to 10. More preferably, these oligosaccharides do not contain substantial amounts (less than 5 weight %) of saccharides outside these DP ranges, and they are soluble. These oligosaccharides may comprise fructo-oligosaccharides (FOS), trans-galacto-oligosaccharides (TOS), xylo-oligosaccharides (XOS), soy oligosaccharides, and the like. Optionally, also higher molecular weight compounds such as inulin, soy polysaccharides, acacia polysaccharides (acacia fibre or arabic gum), cellulose, resistant starch and the like may be incorporated in the composition according to the invention. The amount of insoluble fibre such as cellulose is preferably lower than 20 weight % of the dietary fibre fraction of the composition according to the invention, and/or below 0.6 g/100 ml. The amount of thickening polysaccharides such as carrageenans, xanthans, pectins, galactomannans and other high molecular weight (DP>50) indigestible polysaccharides is preferably low, i.e. less than 20% of the weight of the fibre fraction, or less than 1 g/100 ml. Instead, hydrolysed polysaccharides such as hydrolysed pectins and galactomannans can advantageously be included.

A preferred fibre component is an indigestible oligosaccharide with a chain length (DP) of 2 to 10, for example Fibersol® (resistant oligoglucose), in particular hydrogenated Fibersol®, or a mixture of oligosaccharides having a DP of 2 to 10, such as fructo-oligosaccharides or galacto-oligosaccharides, which may also contain a small amount of higher saccharides (e.g. with a DP of 11 to 20). Such oligosaccharides preferably comprise 50 weight % to 90 weight % of the fibre fraction, or 0.5 g/100 ml to 3 g/100 ml of the composition according to the invention. Other suitable fibre components include saccharides that have only partial digestibility.

In a particular embodiment, the composition according to the invention comprises one or more of fructo-oligosaccharides, inulin, acacia polysaccharides, soy polysaccharides, cellulose and resistant starch.

In another embodiment of the present invention, the composition according to the invention may comprise a mixture of neutral and acid oligosaccharides as disclosed in WO 2005/039597 (N.V. Nutricia), which is incorporated herein by reference in its entirety. More in particular, the acid oligosaccharide has a degree of polymerisation (DP) between 1 and 5000, preferably between 1 and 1000, more preferably between 2 and 250, even more preferably between 2 and 50, most preferably between 2 and 10. If a mixture of acid oligosaccharides with different degrees of polymerisation is used, the average DP of the acid oligosaccharide mixture is preferably between 2 and 1000, more preferably between 3 and 250, even more preferably between 3 and 50. The acid oligosaccharide may be a homogeneous or heterogeneous carbohydrate. The acid oligosaccharides may be prepared from pectin, pectate, alginate, chondroitine, hyaluronic acids, heparine, heparane, bacterial carbohydrates, sialoglycans, fucoidan, fucooligosaccharides or carrageenan, and are preferably prepared from pectin or alginate. The acid oligosaccharides may be prepared by the methods described in WO 01/60378, which is hereby incorporated by reference. The acid oligosaccharide is preferably prepared from high methoxylated pectin, which is characterised by a degree of methoxylation above 50%. As used herein, "degree of methoxylation" (also referred to as DE or "degree of esterification") is intended to mean the extent to which free carboxylic acid groups contained in the polygalacturonic acid chain have been esterified (e.g. by methylation). The acid oligosaccharides are preferably characterised by a degree of methoxylation above 20%, preferably above 50% even more preferably above 70%. Preferably the acid oligosaccharides have a degree of methylation above 20%, preferably above 50% even more preferably above 70%. The acid oligosaccharide is preferably administered in an amount of between 10 mg and 100 gram per day, preferably between 100 mg and 50 grams per day, even more between 0.5 and 20 gram per day.

The term neutral oligosaccharides as used in the present invention refers to saccharides which have a degree of polymerisation of monose units exceeding 2, more preferably exceeding 3, even more preferably exceeding 4, most preferably exceeding 10, which are not or only partially digested in the intestine by the action of acids or digestive enzymes present in the human upper digestive tract (small intestine and stomach) but which are fermented by the human intestinal flora and preferably lack acidic groups. The neutral oligosaccharide is structurally (chemically) different from the acid oligosaccharide. The term neutral oligosaccharides as used in the present invention preferably refers to saccharides which have a degree of polymerisation of the oligosaccharide below 60 monose units, preferably below 40, even more preferably below 20, most preferably below 10. The term monose units refers to units having a closed ring structure, preferably hexose, e.g. the pyranose or furanose forms. The neutral oligosaccharide preferably comprises at least 90%, more preferably at least 95% monose units selected from the group consisting of mannose, arabinose, fructose, fucose, rhamnose, galactose, β-D-galactopyranose, ribose, glucose, xylose and derivatives thereof, calculated on the total number of monose units contained therein. Suitable neutral oligosaccharides are preferably fermented by the gut flora. Preferably the oligosaccharide is selected from the group consisting of: cellobiose (4-O-β-D-glucopyranosyl-D-glucose), cellodextrins ((4-O-β-D-glucopyranosyl)$_n$-D-glucose), B-cyclodextrins (Cyclic molecules of α-1-4-linked D-glucose; α-cyclodextrin-hexamer, β-cyclodextrin-heptamer and γ-cyclodextrin-octamer), indigestible dextrin, gentiooligosaccharides (mixture of β-1-6 linked glucose residues, some 1-4 linkages), glucooligosaccharides (mixture of α-D-glucose), isomaltooligosaccharides (linear α-1-6 linked glucose residues with some 1-4 linkages), isomaltose (6-O-α-D-glucopyranosyl-D-glucose); isomaltriose (6-O-α-D-glucopyranosyl-(1-6)-α-D-glucopyranosyl-D-glucose), panose (6-O-α-D-glucopyranosyl-(1-6)-α-D-glucopyranosyl-(1-4)-D-glucose), leucrose (5-O-α-D-glucopyranosyl-D-fructopyranoside), palatinose or isomaltulose (6-O-α-D-glucopyranosyl-D-fructose), theanderose (O-α-D-glucopyranosyl-(1-6)-O-α-D-glucopyranosyl-(1-2)-B-D-fructofuranoside), D-agatose, D-lyxo-hexulose, lactosucrose (O-β-D-galactopyranosyl-(1-4)-O-α-D-glucopyranosyl-(1-2)-β-D-fructofuranoside), α-galactooligosaccharides including raffinose, stachyose and other soy oligosaccharides (O-α-D-galactopyranosyl-(1-6)-α-D-glucopyranosyl-β-D-fructofuranoside), β-galactooligosaccharides or transgalacto-oligosaccharides (β-D-galactopyranosyl-(1-6)-[β-D-glucopyranosyl]$_n$-(1-4)α-D glucose), lactulose (4-O-β-D-galactopyranosyl-D-fructose), 4'-galatosyllactose (O-D-galactopyranosyl-(1-4)-O-β-D-glucopyranosyl-(1-4)-D-glucopyranose), synthetic galactooligosaccharide (neogalactobiose, isogalactobiose, galsucrose, isolactosel, II and III), fructans-Levan-type (β-D-(2→6)-fructofuranosyl)$_n$ α-D-glucopyranoside), fructans-Inulin-type (β-D-((2→1)-fructofuranosyl)$_n$ α-D-glucopyranoside), 1 f-β-fructofuranosylnystose (β-D-((2→1)-fructofuranosyl)$_n$ B-D-fructofuranoside), xylooligosaccharides (B-D-((1→4)-xylose)$_n$, lafinose, lactosucrose and arabinooligosaccharides.

According to a further preferred embodiment the neutral oligosaccharide is selected from the group consisting of fructans, fructooligosaccharides, indigestible dextrins galactooligosaccharides (including transgalactooligosaccharides), xylooligosaccharides, arabinooligosaccharides, glucooligosaccharides, mannooligosaccharides, fucooligosaccharides and mixtures thereof. Most preferably, the neutral oligosaccharide is selected from the group consisting of fructooligosaccharides, galactooligosaccharides and transgalactooligosaccharides.

Suitable oligosaccharides and their production methods are further described in Laere K. J. M. (Laere, K. J. M., Degradation of structurally different non-digestible oligosaccharides by intestinal bacteria: glycosylhydrolases of *Bi. adolescentis*. PhD-thesis (2000), Wageningen Agricultural University, Wageningen, The Netherlands), the entire content of which is hereby incorporated by reference. Transgalactooligosaccharides (TOS) are for example sold under the trademark Vivinal™ (Borculo Domo Ingredients, Netherlands). Indigestible dextrin, which may be produced by pyrolysis of corn starch, comprises α(1→4) and α(1→6) glucosidic bonds, as are present in the native starch, and contains 1→2 and 1→3 linkages and levoglucosan. Due to these structural characteristics, indigestible dextrin contains well-developed, branched particles that are partially hydrolysed by human digestive enzymes. Numerous other commercial sources of indigestible oligosaccharides are readily available and known to skilled person. For example, transgalactooligosaccharide is available from Yakult Honsha Co., Tokyo, Japan. Soybean oligosaccharide is available from Calpis Corporation distributed by Ajinomoto U.S.A. Inc., Teaneck, N.J.

In a further preferred embodiment the composition according to the invention comprises an acid oligosaccharide with a DP between 2 and 250, prepared from pectin, alginate, and mixtures thereof; and a neutral oligosaccharide, selected from the group of fructans, fructooligosaccharides, indigestible dextrins, galactooligosaccharides including transgalactooligosaccharides, xylooligosaccharides, arabinooligosaccharides, glucooligosaccharides, mannooligosaccharides, fucooligosaccharides, and mixtures thereof.

In a further preferred embodiment the composition according to the invention comprises two chemically distinct neutral oligosaccharides. It was found that the administration of acid oligosaccharides combined with two chemically distinct neutral oligosaccharides provides an optimal synergistic immune stimulatory effect. Preferably the composition according to the invention comprises:

an acid oligosaccharides as defined above;
 a galactose-based neutral oligosaccharide (of which more than 50% of the monose units are galactose units), preferably selected from the group consisting of galactooligosaccharide and transgalactooligosaccharide; and
 a fructose and/or glucose based neutral oligosaccharide (of which more than 50% of the monose units are fructose and/or glucose, preferably fructose units), preferably inulin, fructan and/or fructooligosaccharide, most preferably long chain fructooligosaccharide (with an average DP of 10 to 60).

The mixture of acid- and neutral oligosaccharides is preferably administered in an amount of between 10 mg and 100 gram per day, preferably between 100 mg and 25 grams per day, even more preferably between 0.5 and 20 gram per day.

Viscosity and Osmolarity

In one embodiment of the present invention, the viscosity of the liquid enteral nutritional composition is lower than 120 mPa·s at 20° C. at a shear rate of 100 s$^{-1}$, preferably between 80 and 50 mPa·s, preferably lower than 50 mPa·s, more preferably between 20 and 45 mPa·s. The viscosity may be determined using a rotational viscosity meter using a cone/plate geometry.

In another embodiment of the present invention, the protein comprises of a blend of micellar casein, caseinate and whey, wherein the weight ratio of micellar casein to caseinate ranges from 80:20 to 40:60 and wherein the weight ratio of micellar casein to whey ranges from 95:5 to 70:30. The latter embodiment of the present invention has a viscosity of approximately about 80 mPa·s. This is ideal for orally administering the liquid enteral nutritional composition according to the invention because a person may easily consume a serving having a low viscosity such as that displayed by the present invention. This is also ideal for unit dosages that are tube fed.

In one embodiment of the present invention, the osmolarity of the composition is preferably lower than 900 mOsm/l, more preferably lower than 800 mOsm/l, most preferable lower than 700 mOsm/l.

In one embodiment of the present invention, the density of the composition ranges between 1.05 g/ml and 1.20 g/ml, especially between 1.10 g/ml and 1.18 g/ml.

Dosage Unit

The liquid enteral nutritional composition according to the invention may have the form of a complete food, i.e. it can meet all nutritional needs of the user. As such, it preferably contains 1200 to 2500 kcal per daily dosage. The daily dosage amounts are given with respect to a daily energy supply of 2000 kcal to a healthy adult having a body weight of 70 kg. For persons of different condition and different body weight, the levels should be adapted accordingly. It is understood that the average daily energy intake preferably is about 2000 kcal. The complete food can be in the form of multiple dosage units, e.g. from 4 (250 ml/unit) to 20 (50 ml/unit) per day for an energy supply of 2000 kcal/day using a liquid enteral nutritional composition according to the invention of 2.0 kcal/ml.

The liquid enteral nutritional composition can also be a food supplement, for example to be used in addition to a non-medical food. Preferably as a supplement, the liquid enteral nutritional composition contains per daily dosage less than 1500 kcal, in particular as a supplement, the liquid enteral nutritional composition contains 400 to 1000 kcal per daily dose. The food supplement can be in the form of multiple dosage units, e.g. from 2 (250 ml/unit) to 10 (50 ml/unit) per day for an energy supply of 1000 kcal/day using a liquid enteral nutritional composition according to the invention of 2.0 kcal/ml.

In one embodiment of the present invention, a unit dosage comprises any amount of the liquid enteral nutritional composition according to the invention between 10 ml and 250 ml, the end values of this range included, preferably any amount between 25 ml and 200 ml, the end values of this range included, more preferably any amount between 50 ml and 150 ml, the end values of this range included, most preferably about 125 ml. For example, a person receiving 50 ml unit dosages can be given 10 unit dosages per day to provide nutritional support using a liquid enteral nutritional composition according to the invention of 2.0 kcal/ml. Alternatively a person receiving 125 ml unit dosages can be given 4 or 5 or 6 or 7 or 8 unit dosages per day to provide nutritional support using a liquid enteral nutritional composition according to the invention of 2.0 kcal/ml. Such small dosage units are preferred because of better compliance.

In one embodiment of the present invention, the composition is provided in a ready to use liquid form and does not require reconstitution or mixing prior to use. The composition according to the invention can be tube fed or administered orally. For example, the composition according to the invention can be provided in a can, on spike, and hang bag. However, a composition may be provided to a person in need thereof in powder form, suitable for reconstitution using an aqueous solution or water such that the composition according to the invention is produced. Thus in one embodiment of the present invention, the present composition is in the form of a powder, accompanied with instructions to dissolve or reconstitute in an aqueous composition or water to arrive at the liquid nutritional enteral composition according to the present invention. In one embodiment of the present invention, the present liquid nutritional enteral composition may thus be obtained by dissolving or reconstituting a powder, preferably in an aqueous composition, in particular water.

In one embodiment of the present invention, the composition according to the invention is packaged. The packaging may have any suitable form, for example a block-shaped carton, e.g. to be emptied with a straw; a carton or plastic beaker with removable cover; a small-sized bottle for example for the 80 ml to 200 ml range, and small cups for example for the 10 ml to 30 ml range. Another suitable packaging mode is inclusion of small volumes of liquid (e.g. 10 ml to 20 ml) in edible solid or semi-solid hulls or capsules, for example gelatine-like coverings and the like. Another suitable packaging mode is a powder in a container, e.g. a sachet, preferably with instructions to dissolve or reconstitute in an aqueous composition or water.

Preparation

The liquid enteral nutritional composition according to the invention may be prepared by first preparing the liquid protein composition. This may be done by sequentially or simultaneously dissolving micellar casein in powder form and caseinate in powder form in water. It is also possible to use micellar casein in a wet form, directly prepared from milk. It may even be advantageous to prepare the micellar casein as a part of a continuous process to prepare the composition according to the invention. The latter may be done in the same production facility to prepare the composition according to the invention.

Furthermore, if the liquid enteral nutritional composition is to contain further components, a nutritional product may be prepared by subsequently adding the carbohydrates to the protein composition, followed by adding the water-soluble vitamins and other components in one or two stages, mixing, adjusting the resulting composition to the desired viscosity, adding the fat, including fat-soluble vitamins, homogenizing, subjecting the resulting solution to a heat-treatment (pasteurization, sterilisation) and packaging the resulting product. In this respect, it is noted that the acidity of the composition is very important during the heat-treatment. The pH should be between about 6.6 and 7.2 for the pasteurisation and sterilisation. Typical pasteurisation times are 30 sec at 85° C. Typical sterilisation times are 4 minutes at 124° C.

In the embodiment where micellar casein, caseinate and whey is present in the formulation according to the invention, it was found favorable not to pasteurise but only to sterilise the formulation according to the invention.

Effectivity

The present invention also concerns a method of providing nutrition to a person in need thereof, comprising the steps of administering to said person the nutritional composition according to the present invention. Said person may be an elderly person, a person that is in a disease state, a person that is recovering from a disease state, or a person that is malnourished.

In a further aspect, the present invention also concerns the simultaneous or sequential use of micellar casein and caseinate in the manufacture of a liquid nutritional composition according to the present invention for providing enteral nutrition to a person in need thereof. In one particular embodiment of the present invention, said composition provides 6 to 14 g of protein per 100 ml of composition, said protein including micellar casein, caseinate and optionally whey, the composition having an energy density of at least 2.0 kcal/ml. In another particular embodiment of the present invention, said protein provides 10% to 30% of the total energy content of the composition, the composition having an energy density of at least 2.0 kcal/ml.

In one embodiment, the present invention concerns a liquid enteral nutritional composition comprising:

a) about 9.6 g of protein per 100 ml of the composition of a mixture of micellar casein and caseinate, with a weight ratio of micellar casein to caseinate of about 65:35, said protein providing about 16% of the total energy content of the composition;

b) fat providing about 35% of the total energy content of the composition;

c) carbohydrate providing about 49% of the total energy content of the composition, said composition having an energy density of about 2.4 kcal/ml.

In another embodiment, the present invention concerns a liquid enteral nutritional composition comprising:

a) about 9.6 g of protein per 100 ml of the composition of a mixture of micellar casein, caseinate and whey with a weight ratio micellar casein:caseinate:whey of about 44:45:11, said protein providing about 16% of the total energy content of the composition;

b) fat providing about 35% of the total energy content of the composition;

c) carbohydrate providing about 49% of the total energy content of the composition, said composition having an energy density of about 2.4 kcal/ml.

In yet another embodiment, the present invention concerns a liquid enteral nutritional composition comprising:

a) about 9.6 g of protein per 100 ml of the composition of a mixture of micellar casein, caseinate and whey with a weight ratio micellar casein:caseinate:whey of about 63:21:16, said protein providing about 16% of the total energy content of the composition;

b) fat providing about 35% of the total energy content of the composition;

c) carbohydrate providing about 49% of the total energy content of the composition, said composition having an energy density of about 2.4 kcal/ml.

EXAMPLES

The following composition according to the invention has been prepared (Table 1). The composition is produced in a manner known per se, e.g. by mixing the ingredients, without difficulties, is shelf-stable, has desirable organoleptic properties, has a very high nutrient density and is effective for a person in need thereof It should be understood that various changes and modifications to the presently preferred embodiments described herein will be apparent to those skilled in the art. Such changes and modifications may be made without departing from the spirit and scope of the invention and without diminishing its advantages.

Notes to the Table

Skim concentrated milk contains about 13.3% of micellar casein and whey in a ratio of about 80:20.

Milk Protein Isolate contains about 89% of micellar casein and whey in a ratio of about 80:20.

Micellar Casein Isolate contains about 89% of micellar casein and whey in a ratio of about 95:5.

TABLE 1

| Component | Amount per 100 ml of product | Amount per 100 ml of product | Amount per 100 ml of product | Amount per 100 ml of product | Amount per 100 ml of product | Amount per 100 ml of product | Amount per 100 ml of product |
|---|---|---|---|---|---|---|---|
| Energy | 240 kcal | 240 kcal | 240 kcal | 240 kcal | 240 kcal | 240 kcal | 240 kcal |
| Protein | 16.0 En % | 16.0 En % | 16.0 En % | 16.0 En % | 16.0 En % | 16.0 En % | 16.0 En % |
| Protein | 9.6 g | 9.6 g | 9.6 g | 9.6 g | 9.6 g | 9.6 g | 9.6 g |
| Skim concentrated milk* | — | 4.07 g | 4.07 g | 3.49 g | 3.49 g | — | — |
| Potassium caseinate | — | 2.71 g | 2.64 g | 2.11 g | 2.11 g | — | — |
| Calcium caseinate | — | 1.66 g | — | — | — | — | — |
| Sodium-caseinate | 3.3 g | — | — | — | — | 3.3 g | 3.3 g |
| Milk Protein Isolate* | — | 1.25 g | 3.04 g | 4.11 g | — | — | — |
| Micellar Casein Isolate* | 6.3 g | — | — | — | 4.11 g | 6.3 g | 6.3 g |
| Native micellar casein | 6.0 | 4.26 | 5.68 | 6.08 | 6.70 | 6.0 | 6.0 |
| Caseinate | 3.3 | 4.37 | 2.64 | 2.11 | 2.11 | 3.3 | 3.3 |
| Whey | 0.3 | 1.06 | 1.42 | 1.52 | 0.90 | 0.3 | 0.3 |
| Fat | 35 En % | 35 En % | 35 En % | 35 En % | 35 En % | 35 En % | 35 En % |
| Fat mainly comprising canola oil | 9.3 g | 9.3 g | 9.3 g | 9.3 g | 9.3 g | 9.3 g | 9.3 g |
| Carbohydrates | 49 En % | 49 En % | 49 En % | 49 En % | 49 En % | 49 En % | 49 En % |
| maltodextrose (DE47) | 29.4 g | 29.4 g | 29.4 g | 29.4 g | 29.4 g | 9.8 g | 9.8 g |
| sucrose | — | — | — | — | — | 9.8 g | 9.8 g |
| trehalose | — | — | — | — | — | 9.8 g | 9.8 g |
| Dietary Fibre | — | — | — | — | — | 0.9 g GOS<br>0.1 g lcFOS<br>0.2 g low viscosity pectin | 1.23 g inuline<br>1.72 g FOS<br>0.41 g cellulose<br>0.086 g resistant starch |
| Viscosity (mPa·s at 20° C. at 100 s$^{-1}$) | 70 mPa·s | 110 mPa·s | 80 mPa·s | 80 mPa·s | 75 mPa·s | — | — |
| Density | 1.16 g/ml | 1.16 g/ml | 1.16 g/ml | 1.16 g/ml | 1.16 g/ml | — | — |
| Unit dosage | 125 ml | 125 ml | 125 ml | 125 ml | 125 ml | 125 ml | 125 ml |

Minerals and vitamines are added as 16% of RDI.

The invention claimed is:

1. A heat-treated liquid enteral nutritional obtainable by heat-treating a liquid enteral nutritional composition having an energy density of at least 2.0 kcal/ml and comprising 8 to 14 g of protein per 100 ml of the composition, the protein comprising micellar casein and caseinate in weight ratio of micellar casein to caseinate ranging from 90:10 to 55:45.

2. The liquid enteral nutritional composition according to claim 1, wherein the combined amount of micellar casein and caseinate is at least 70 weight % of the total protein.

3. The liquid enteral nutritional composition according to claim 1, further comprising whey.

4. The liquid enteral nutritional composition according to claim 3, wherein the combined amount of micellar casein and caseinate is at least 70 weight % of the total protein.

5. The liquid enteral nutritional composition according to claim 4, comprising up to 30 weight % of whey based on total protein.

6. The liquid enteral nutritional composition according to claim 5, wherein the combined amount of micellar casein, caseinate and whey is at least 95 weight % of the total protein.

7. The liquid enteral nutritional composition according to claim 1, wherein the composition has an energy density of at least 2.4 kcal/ml.

8. The liquid enteral nutritional composition according to claim 1, wherein the caseinate is Na-caseinate, Ca-caseinate, Mg-caseinate, K-caseinate or any mixture or combination thereof.

9. The liquid enteral nutritional composition according to claim 1, wherein the weight ratio of micellar casein to whey ranges from 95:5 to 70:30.

10. The liquid enteral nutritional composition according to claim 1, further comprising fat, the fat providing between 20 to 40% of the total energy content of the composition.

11. The liquid enteral nutritional composition according to claim 1, further comprising carbohydrate, the carbohydrate providing between 30 to 60% of the total energy content of the composition.

12. The liquid enteral nutritional composition according to claim 1, further comprising at least one acid.

13. The liquid enteral nutritional composition according to claim 1, wherein the viscosity of the composition is lower than 120 mPa·s as measured at a shear rate of $100\,s^{-1}$ at 20° C. using a rotational viscosity meter using a cone/plate geometry.

14. The liquid enteral nutritional composition according to claim 1, further comprising one or more of fructo-oligosaccharides, inulin, acacia polysaccharides, soy polysaccharides, cellulose and resistant starch.

15. The liquid enteral nutritional composition according to claim 1, further comprising (i) an acid oligosaccharide with an average degree of polymerisation between 2 and 250, prepared from pectin, alginate and mixtures thereof; and (ii) a neutral oligosaccharide, selected from the group of fructans, fructooligosaccharides, indigestible dextrins, galactooligosaccharides including transgalactooligosaccharides, xylooligosaccharides, arabinooligosaccharides, glucooligosaccharides, mannooligosaccharides, fucooligosaccharides, and mixtures thereof.

16. The liquid enteral nutritional composition according to claim 15, comprising a mixture of low viscosity pectin with an average degree of polymerisation of 2 to 250, a galactose-based neutral oligosaccharide, and a long chain fructose-based oligosaccharide with an average degree of polymerisation of 10 to 60.

17. The method according to claim 15, wherein the composition is sterilized and/or pasteurized.

18. The method according to claim 17, wherein the composition is sterilized.

19. The method according to claim 15, wherein the composition has an energy density of at least 2.4 kcal/ml.

20. The method according to claim 15, wherein the composition comprises at least 85 weight % of a combination of micellar casein and caseinate.

21. The liquid enteral nutritional composition according to claim 1, having an energy density of 2.4 kcal/ml, and comprising:
(a) 9.6 g of protein per 100 ml of the composition of a mixture of micellar casein and caseinate with a weight ratio of 65:35, the protein providing 16% of the total energy content of the composition;
(b) fat, the fat providing 35% of the total energy content of the composition; and
(c) carbohydrate, the carbohydrate providing 49% of the total energy content of the composition.

22. The liquid enteral nutritional composition according to claim 1, having an energy density of 2.4 kcal/ml, and comprising:
(a) 9.6 g of protein per 100 ml of the composition of a mixture of micellar casein, caseinate and whey, optionally with a weight ratio micellar casein:caseinate:whey of 44:45:11, the protein providing 16% of the total energy content of the composition;
(b) fat, the fat providing 35% of the total energy content of the composition;
(c) carbohydrate, the carbohydrate providing 49% of the total energy content of the composition.

23. The liquid enteral nutritional composition according to claim 1, wherein the composition is sterilized and/or pasteurized.

24. A method of providing nutrition to a person in need thereof, comprising administering to the person a composition according to claim 1.

25. The method according to claim 24, wherein the person in need thereof is an elderly person having an age of 50 years or more, a person that is in a disease state, a person that is recovering from a disease state, or a person that is malnourished.

26. The liquid enteral nutritional composition according to claim 1, wherein the protein provides between 15 to 30% of the total energy content of the composition.

27. The liquid enteral nutritional composition according to claim 1, wherein the composition comprises at least 85 weight % of the combination of micellar casein and caseinate.

28. The liquid enteral nutritional composition according to claim 1, wherein the composition comprises between 155 and 185 mg/100 ml calcium.

29. The liquid enteral nutritional composition having an energy density of 2.4 kcal/ml and comprising:
(a) 9.6 g of protein per 100 ml of the composition of a mixture of micellar casein, caseinate and whey, optionally with a weight ratio micellar casein:caseinate:whey of 63:21:16, the protein providing 16% of the total energy content of the composition;
(b) fat, the fat providing 35% of the total energy content of the composition;
(c) carbohydrate, the carbohydrate providing 49% of the total energy content of the composition, the composition.

30. A method for manufacturing a heat-treated liquid enteral nutritional composition, comprising heat-treating a liquid enteral nutritional composition having an energy density of at least 2.0 kcal/ml and comprising 8 to 14 g of protein per 100 ml of the composition, wherein the protein comprises micellar casein and caseinate in a weight ratio of micellar casein to caseinate ranging from 90:10 to 55:45.

31. The method according to claim 30, wherein the protein provides between 15 to 30% of the total energy content of the composition.

32. The method according to claim 30, wherein the composition comprises up to 15 weight % of whey based on total protein.

* * * * *